(12) United States Patent
Karlsson et al.

(10) Patent No.: US 6,494,873 B2
(45) Date of Patent: Dec. 17, 2002

(54) ABSORBENT ARTICLE PROVIDED WITH A BELT

(75) Inventors: Katharina Karlsson, Härryda (SE); Kent Hermansson, Västra Frölunda (SE)

(73) Assignee: SCA Hygiene Products, Göteborg (SE)

( * ) Notice: Subject to any disclaimer, the term of this patent is extended or adjusted under 35 U.S.C. 154(b) by 0 days.

(21) Appl. No.: 09/816,174

(22) Filed: Mar. 26, 2001

(65) Prior Publication Data

US 2001/0034512 A1 Oct. 25, 2001

Related U.S. Application Data

(60) Provisional application No. 60/201,288, filed on May 2, 2000.

(51) Int. Cl.[7] .................................................. A61F 13/15
(52) U.S. Cl. ........................ 604/392; 604/394; 604/396; 604/386
(58) Field of Search ..................... 604/385.01, 386, 604/387, 392, 394, 396

(56) References Cited

U.S. PATENT DOCUMENTS 2,910,982 A  *  11/1959  Woodward .................. 128/284

FOREIGN PATENT DOCUMENTS

| EP | 287388 | 10/1988 |
|----|--------|---------|
| EP | 409307 | 1/1991 |
| EP | 463276 | 1/1992 |
| EP | 605012 | 7/1994 |
| FR | 2586558 | 3/1987 |
| WO | 8604812 | 8/1996 |

* cited by examiner

*Primary Examiner*—Dennis Ruhl
*Assistant Examiner*—Jacqueline F Stephens
(74) *Attorney, Agent, or Firm*—Burns, Doane, Swecker & Mathis, LLP

(57) ABSTRACT

Absorbent article such as a diaper and an incontinence guard comprising a pair of belt portions (9) attached to the rear portion (6) of the article and which are intended to be fastened together around the waist of the wearer and where said front portion (5) is provided with attachment means (8) intended to be attached to the belt portions (9), in such a way that the article will assume a pantlike shape, where the belt portions (9) form a part of the waist portions of the pant. The belt portions (9) are before use folded in accordion-like fashion and each form an accordion-like folded package (11) which is arranged in a pocket (12) at each side edge of the rear portion (6) of the absorbent article, and can be extended from said pocket and unfolded when the article is to be used, after which the belt portions may be fastened together around the waist of the wearer.

4 Claims, 3 Drawing Sheets

ABSORBENT ARTICLE PROVIDED WITH A BELT

This application claims the benefit of provisional application 60/201,288 filed May 2, 2000.

TECHNICAL FIELD

The present invention refers to an absorbent article such as a diaper and an incontinence guard comprising a liquid permeable topsheet, a liquid impermeable backsheet and an absorbent body enclosed therebetween, said article having a front portion, a rear portion and a crotch portion therebetween, and further is provided with a pair of belt portions attached to the rear portion of the article and which are intended to be fastened together an sound the waist of the wearer and where said front portion is provided with attachment means intended to be attached to the belt portions, in such a way that the article will assume a pantlike shape, where the belt portions form a part of the waist portions of the pant.

BACKGROUND OF THE INVENTION

Diapers and incontinence guards for incontinent adults usually have a garment portion holding an absorbent body in place against the user's body and attachment means which hold the garment portion in place also when the user is moving. A common type of attachment means are adhesive tapes or hook and loop fasteners of the touch-and-close type which directly attach the front and rear portions of the absorbent article to each other. It is her known, through e.g. EP-A-0 287 388, EP-A-0 409 307, EP-A-0 605 012 and PR-A-2 596 558, to attach the front and rear portions of the article by means of a belt, at which the possibilities to adjust the fit are improved. The belt further provides a simplified change of diaper or incontinence guard. The ends of the belt portions can however be difficult to grasp when the article shall be applied to a wearer, especially if the wearer is lying down and the belt ends get caught under the wearer.

Through WO 86/04812 it is previously known to fold the attachment straps of a diaper, i.e. the straps that carry the attachment means that fasten up the front and rear portions of the diaper, in accordion-like fashion before they are applied to the diaper in order to simplify manufacture and packaging of the products. The folded attachment straps are kept together by a weak adhesive applied in narrow zones in order to be easily released and unfolded when the diaper is ready for use. The attachment straps do however not constitute a belt as defined in the present invention.

Through EP-A-0 463 276 it is previously known to keep extensible fastener tabs in pockets at each side edge at the rear portion of the diaper. The fastener tabs are elastic and can when used be extended and starched from the pockets. Neither in this case the fastener tabs constitute a belt which is to be attached around the waist of the user.

OBJECT AND MOST IMPORTANT FEATURES OF THE INVENTION

The object of the present invention is to accomplish a belt-provided absorbent article, such as a diaper or incontinence guard, in which the application of the product on the user is simplified by the fact that the belt portions during application are easily accessible even if the user is lying down. This has according to the invention been solved by the fact that the belt portions before use are folded in accordion-like fashion and each form an accordion-like folded package which is arranged in a pocket at each side edge of the rear portion of the absorbent article, and can be extended from said pocket and unfolded when the article is to be used, after which the belt portions may be fastened together around the waist of the wearer.

According to a preferred embodiment said pocket is formed between the liquid pervious topsheet and the liquid impervious backsheet of the rear portion.

Preferably the accordion folds of the belt portions are kept together by easily breakable seals.

DESCRIPTION OF DRAWINGS

The invention will in the following be closer described with reference to an embodiment shown in the accompanying drawings.

DESCRIPTION OF AN EMBODIMENT

Figure 1:
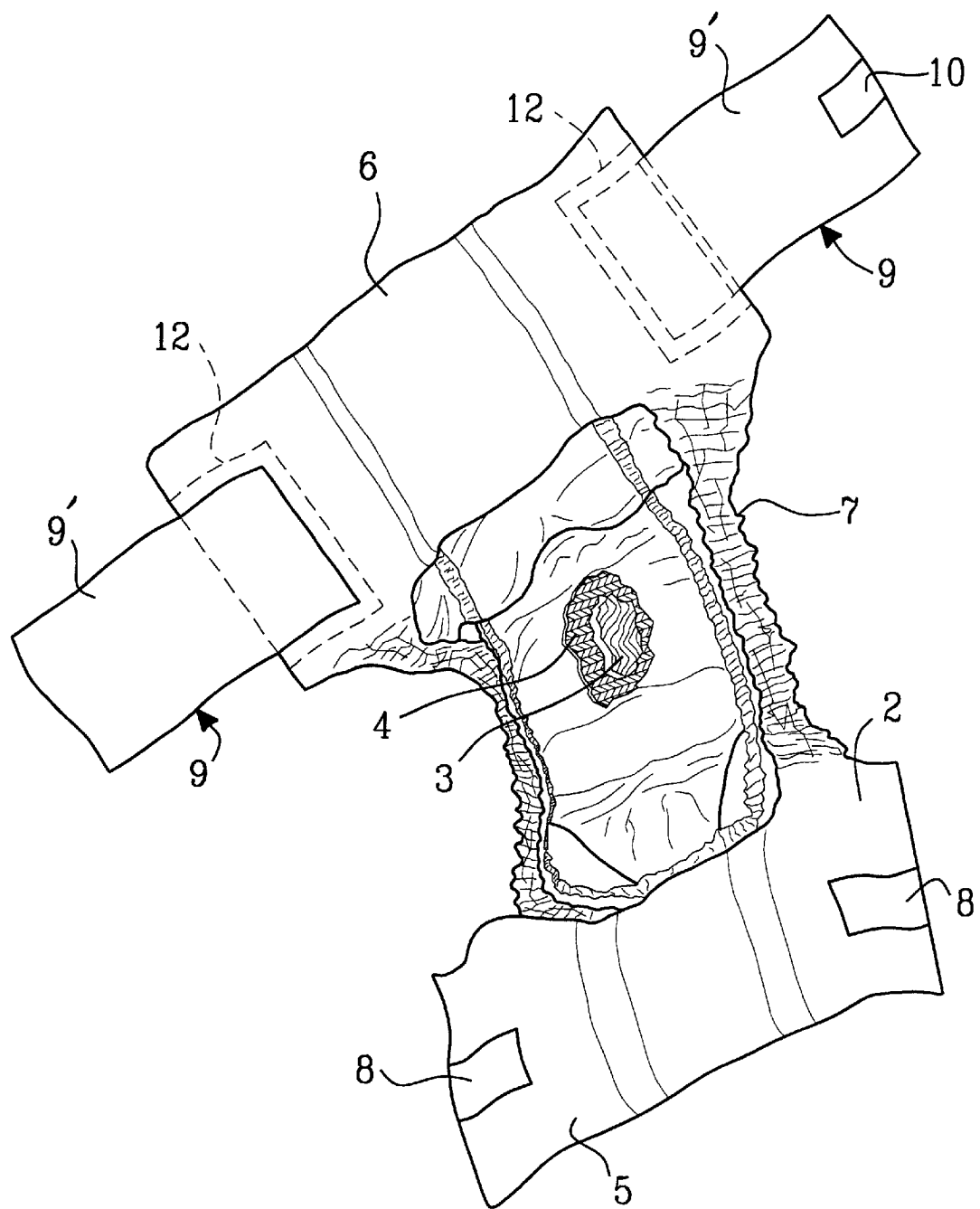
FIG. 1 shows schematically a perspective view of a diaper or incontinence guard according to the invention having the belt portions folded and placed in pockets an the rear portion.
Figure 2:
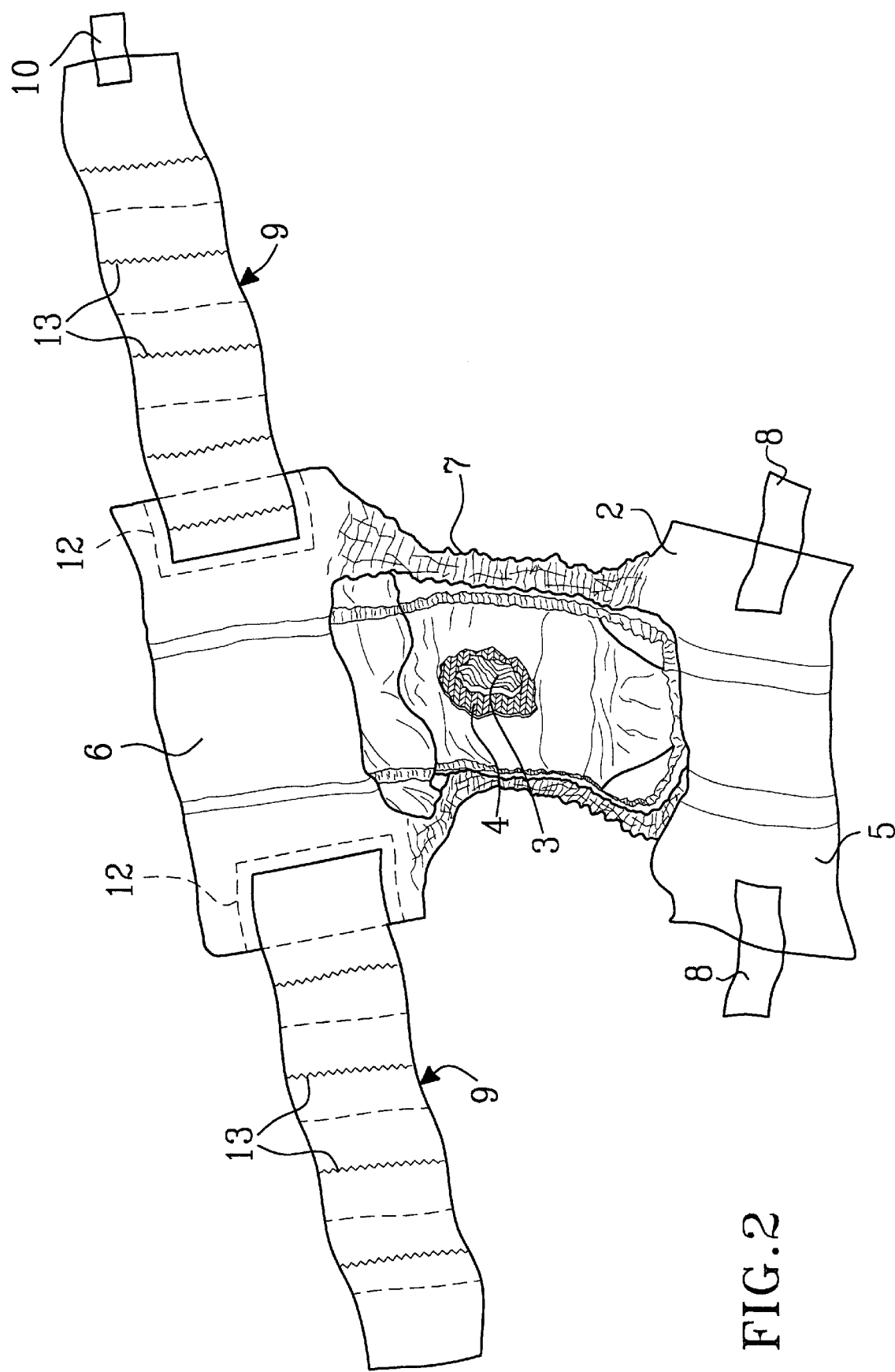
FIG. 2 shows the diaper according to FIG. 1 but having the belt portions extended and unfolded.
Figure 3:
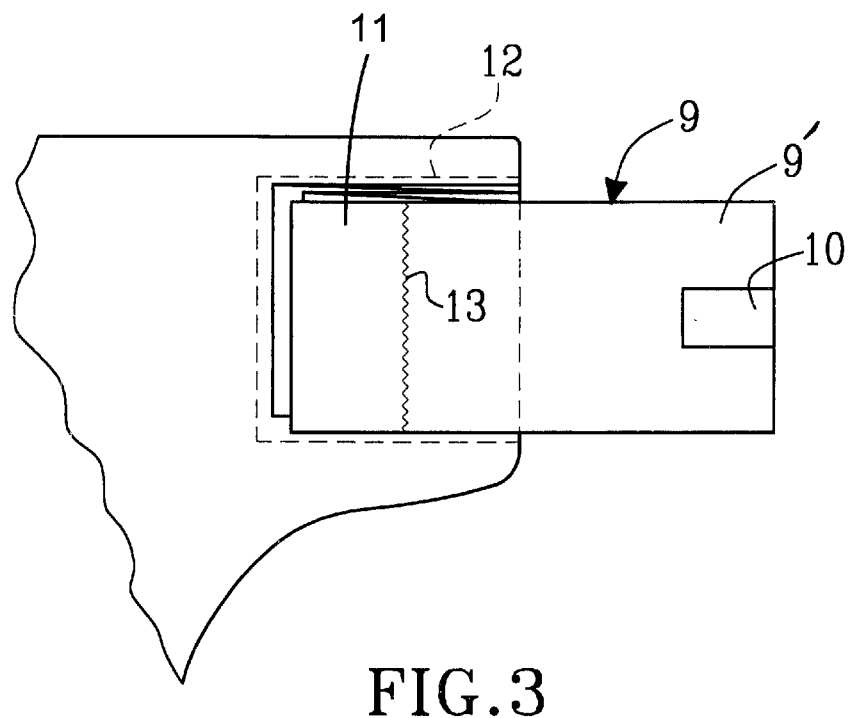
FIGS. 3 and 4 show on a larger scale one of the belt portions in folded and unfolded positions respectively.
Figure 4:
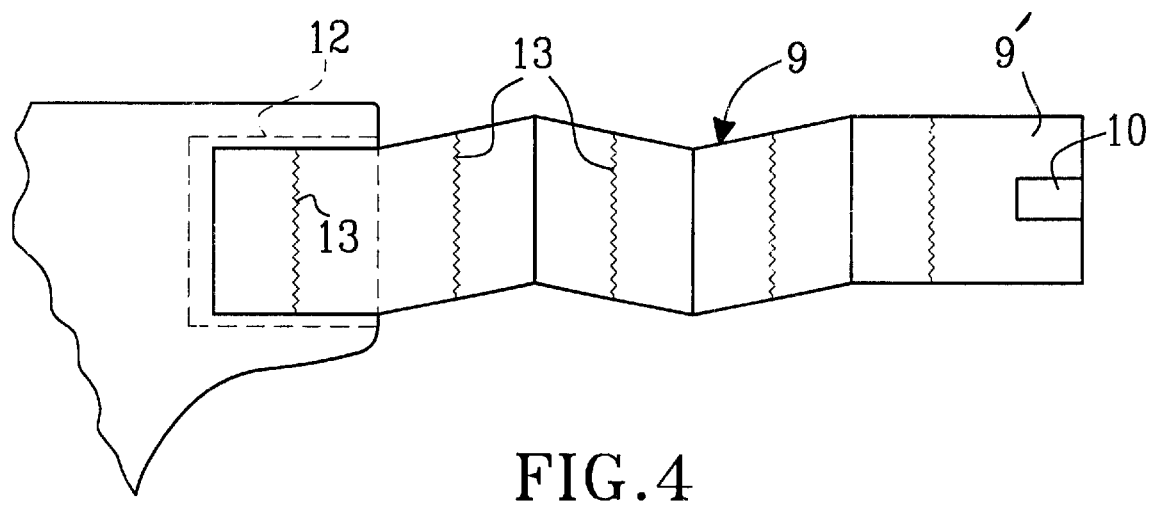

The drawing shows an embodiment of a diaper or incontinence guard 1 comprising a liquid permeable topsheet 2, a liquid impermeable backsheet 3 and an absorbent body 4 enclosed therebetween. The liquid permeable topsheet 2 can consist of a nonwoven material, e.g. a spunbond material of continuous filaments, a meltblown material or a bonded carded fibrous web. The liquid impermeable backsheet 3 may consist of a plastic film, a nonwoven material coated with a liquid impervious material or a hydrophobic nonwoven material which resists liquid penetration.

The topsheet 2 and the backsheet material 3 has a somewhat greater extension in the plane than the absorbent body 4 and extends outside the edges thereof. The layers 2 and 3 are connected to each other within the projecting portions thereof, e.g. by gluing or welding by heat or ultrasonic.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwovens or the like. It is common to combine cellulosic fluff pulp with superabsorbents in an absorbent body. It is also common to have absorbent bodies comprising layers of different material with different properties with respect to liquid acquisition capacity, liquid distribution capacity and storage capacity. It is well-known to the person skilled in the art and does therefore not have to be described in detail. The Win absorbent bodies which are common in for example baby diapers and incontinence guards often comprise a compressed mixed or layered structure of cellulosic fluff pulp and superabsorbent.

The diaper/incontinence guard is inttended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The front portion 5 is provided with a pair of adhesive tape portions 8 or other type of attachment means such as hooks and loops fasteners of the touch-and-close type.

A pair of belt portions 9 are with one end attached, e.g. glued or ultrasonically welded, to the rear portion 5 of the diaper. The belt portions 9 are with their opposite ends intended to be fastened together, e.g. by means of tape tab 10 which is taped against the outside of the opposite belt portion. Instead of a tape tab there may be another optional attachment means, such as hook-and-loop type fasteners, The attachment tapes 8 of the front portion 5 or corresponding attachment means are intended to be attached against the outsides of the belt portions 9 in order to fasten together the diaper/incontinence guard to the desired pantlike shape.

The width of the belt portions 9 should be between 5–20 cm, preferably, between 7–15 cm.

The belt portions 9 are preferably a laminate of a carrier material, which forms the outside of the belt, and a soft nonwoven, which forms the inside of the belt intended to be in direct contact with the skin of the user.

A suitable nonwoven material can be a spunbond material of e.g. polypropylene or polyethylene fibres. Conjugate fibres may also be used. Another suitable nonwoven material can be a carded thermobonded material of e.g. polypropylene-, polyester- or conjugate fibres.

As a carrier material there can be used a plastic film or another appropriate material, e.g. a nonwoven. The carrier material should be adapted to function as a reception surface for the attachment means 8 and 10, at which in those cases the attachment means are tape tabs, a plastic film is suitable. In case other types of attachment means are used instead of tape tabs, e.g. hook-and-loop type fasteners, another type of carrier material is suitable which may function as a reception surface for the attachment ineans in question. Also elastic laminates are suitable to use as material in the belt portions.

The belt portions 9 are before use folded in accordion-like fashion and each form an accordion-like folded package 11 arranged in pocket 12 at each side edge of the rear portion 6 of the. diaper/incontinence guard. A flap 9 of each belt portion 9 projects preferably outside the pocket 12, so that it may easily be grasped. This pocket 12 preferably constitutes a space between the topsheet 2 and the backsheet material 3 where these are not joined together. The pocket may also constitute a separate part attached on the outside of the backsheet material 3 alternatively on the inside of the topsheet material 2.

The accordion folds 9 of the belt portions are kept together by means of easily breakable seals 13, e g glue strings/glue spots or weld seams/weld spots provided by ultrasonic or heat. When the diaper/incontinence guard is to be applied on the user the belt portions 9 are easily accessible for the nursing staff and by a light jerk in the flap 9 projecting from pocket 12 the seal is broken and the belt portions 9 can be unfolded and attached around the waist of the user. The tape tabs 8 of the front portion 5 or corresponding attachment means can then be attached against the outside of the belt portions 9 in order to fasten together the diaper/incontinence guard to the desired pantlike shape.

The invention is of course not limited to the above described embodiment but can be modified within the scope of the claims

What is claimed is:

1. An absorbent article comprising a liquid permeable topsheet, a liquid impermeable backsheet and an absorbent body enclosed therebetween, said article having a front portion, a rear portion and a crotch portion therebetween, and further is provided with a pair of belt portions attached to the rear portion of the article and which are intended to be fastened together around a waist of a wearer and where said front portion is provided with attachment means intended to be attached to the belt portions, in such a way that the article will assume a pant shape, where the belt portions form a part of waist portions of the pant, wherein the belt portions before use are folded in accordion-like fashion and each form an accordion-like folded package which is arranged in a pocket at each side edge of the rear portion of the absorbent article, and can be extended from said pocket and unfolded when the article is to be used, after which the belt portions may be fastened together.

2. The absorbent article as claimed in claim 1, wherein said pocket is formed between the liquid pervious topsheet and the liquid impervious backsheet of the rear portion.

3. The absorbent article as claimed in claim 1, wherein the accordion folds of the belt portions are kept together by easily breakable seals.

4. The absorbent article as claimed in claim 1, wherein the absorbent article is a diaper or an incontinence guard.

* * * * *